United States Patent [19]
Comber et al.

[11] Patent Number: 5,767,140
[45] Date of Patent: Jun. 16, 1998

[54] 5,5-DISUBSTITUTED HYDANTOINS

[75] Inventors: Robert N. Comber, Savannah, Ga.; Robert C. Reynolds, Birmingham, Ala.; Robert W. Buckheit, Jr., Myersville, Md.

[73] Assignee: Southern Research Institute, Birmingham, Ala.

[21] Appl. No.: 403,339

[22] Filed: Mar. 14, 1995

Related U.S. Application Data

[63] Continuation-in-part of Ser. No. 945,208, Sep. 15, 1992, abandoned.

[51] Int. Cl.$^6$ ............................................. A01N 43/50
[52] U.S. Cl. .................... 514/389; 548/311.4; 435/238
[58] Field of Search ............................. 435/238; 514/389

[56] References Cited

U.S. PATENT DOCUMENTS 3,547,948 12/1970 Shen et al. ............................. 514/389
3,655,692 4/1972 Shen et al. ............................. 514/389

OTHER PUBLICATIONS

Rodgers et al. *J. Med. Chem* 20(4) 1977 pp. 591–594.

Comber et al. *J. Med. Chem* 35(19) 1992 pp. 3567–3572.

*Primary Examiner*—Leon B. Lankford, Jr.
*Attorney, Agent, or Firm*—Yahwak & Associates

[57] ABSTRACT

A series of 5,5-disubstituted Hydantoin derivatives synthesized by alkylating 5,5-bis(thiomethyl)-2,4-imidazolidinedione with halomethyl aromatic or halomethyl heteroaromatic precursors or by using the Buchener-Berg procedure on the required ketone. This series of 5,5-disubstituted Hydantoin derivatives are biologically active in their ability to inhibit HIV-induced death and virus production in mammalian (human) cells.

14 Claims, No Drawings

5,5-DISUBSTITUTED HYDANTOINS

The present application is a Continuation in Part of our earlier U.S. patent application Ser. No. 07/945,208 filed Sep. 15th 1992, now abandoned which in turn was filed in the United States Receiving Office as International Patent Application PCT/US93/08627 on Sep. 14th 1993.

Partial support for the research which led to the making of the present invention was provided by funds from the United States National Institutes of Health through the national Cooperative Drug Discovery Group Program. Accordingly, the United States Government has certain statutory rights to this invention under 35 U.S.C. §200 et seq.

Many strategies have been utilized in the design of new chemotherapeutic agents for the treatment of AIDS. Generally, new compounds have been designed to interfere with any of a number of key steps In the replicative cycle of the human immunodeficiency virus (HIV), the causative agent for this life-threatening disease. One strategy that has provided a number of promising compounds has been the disruption of virus adsorption to the host-cell membrane. This interaction is known to rely on an affinity of the viral-encoded glycoprotein, gp120, for the cellular CD-4 receptor of the host.

Compounds that have been shown to interfere with this Interaction include soluble forms of CD-4, aurintricarboxylic acid, and various sulfated polysaccharides.

In 1986, Lehr and Zimmer reported that diphenylhydantoin (dilantin, Compound 1), according to the following structure:

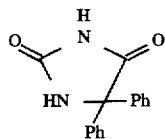

best known as a membrane-reactive drug that has been conventionally used in antiepileptic therapy for some 40 years, inhibits HIV binding to CD-4 positive lymphocytes. More recently, these findings have been extended to suggest that this inhibition is likely due to host-cell membrane fluidization resulting in a reduced availability of the CD-4 receptor for ligand interaction [see Virology 179:609 (1990) ]. As a complement to this work, it has been demonstrated that dilantin suppresses the influx of $Ca^{+2}$ ions that occurs shortly after HIV infection. This suggests a possible role of membrane-associated calcium-dependent cellular processes in HIV infection [see Virology 173:581 (1989), and DMW Dtsch. Med. Wochenschr. 111:1001(1986)].

For several years we have had an interest In developing anti-AIDS drugs by targeting certain biological processes associated with the HIV glycoprotein coat. We have previously synthesized and reported on a number of polysaccharides that were designed to interfere with the biosynthesis of gp120. Similar approaches were used by others to obtain such potent anti-HIV compounds as N-butyldeoxynojirimycin and related glycosylation inhibitors.

The present invention describes a series of hydantoin derivatives related to dilantin that were prepared as a result of discovering anti-HIV activity in 5,5-bis[[(phenylmethyl) thio]methyl]-2,4-imidazolindinedione (compound 2), a related compound according to the structure:

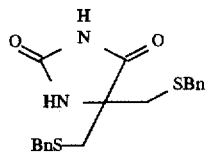

The structures of the compounds according to the present invention, are shown in Table 1. The starting material for the synthesis of most of these compounds was 5,5-bis (thiomethyl)-2,4-imidazolindinedione (Compound 3), a compound according to the structure:

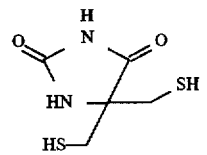

which was readily obtained from the known 5,5-bis [[(phenylmethyl)thio]methyl]-2,4-imidazolidinedione (Compound 2). The remaining compounds according to the present invention were prepared from the appropriate ketones using the Buchener-Berg procedure [see J. Med. Chem. 20:591 (1977)]. Thus, compound 2 was converted into the key intermediate (Compound 3) by treatment with sodium in liquid ammonia followed by chromatographic purification. For the synthesis of hydantoin compounds 4b-o according to the present invention, compound 3 was treated with 3 equivalents of NaOEt followed by 2 equivalents of the required alkylating agents, which were all commercially available with the exception of 2-(chloromethyl)thiophene used in the preparation of compound 4m. Compound 4n was obtained by reducing the nitro group in 4h with granular tin in HCl. Compound 2 was treated with $P_2S_5$ to obtain the 2,4-dithioxohydantoin derivative, compound 6. Monoalkylated hydantoin compound 8 was obtained by treating the trianion of 3 drop-wise at 0° C. with only 1 equivalent of benzyl bromide followed by chromatography to remove any remaining compound 2 that formed. The unsymmetrical hydantoin of compound 9 was formed by alkylating the dianion of compound 8 with 2-bromoethanol. The only other unsymmetrical hydantoin, the hydantoin of S-benzylcysteine (compound 7) was synthesized according to protocols in the literature. Compound 10 was synthesized by barium hydroxide hydrolysis of compound 2.

As noted previously, the Buchener-Berg method was used to synthesize several of the compounds according to the present invention. Hydantoins 5a and 5b were synthesized from 1,3-dichloro-2-propanone by initial displacement reaction with 4-mercaptopyridine or thiophenol, respectively, followed by treatment of the resultant ketones with potassium cyanide and ammonium carbonate. Compound 4a, in which the side-chain heteroatom atom is oxygen instead of sulfur, was formed in an analogous fashion from 1,3-bis (benzyloxy)-2-propanone.

A further, more detailed and complete understanding of the present invention can be had by reference to the following examples. In these examples, melting points were determined on a Mel-Temp apparatus and are uncorrected. The alkylating agents used in the synthesis of compounds 4b-o were all commercially available. Chromatography column sizes are given as width x length.

To more understand the compounds according to the present invention, compounds 2, 3 and 4a-o all have the following general structure:

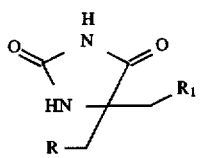

wherein the meanings for R and $R_1$ may be found in Table 1; compounds 5a and 5b all have the following general structure:

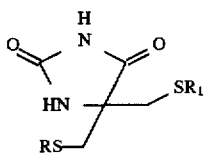

wherein the meanings for R and $R_1$ may be found in Table 1; compound 6 has the following general structure:

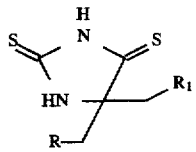

wherein the meanings for R and $R_1$ may be found in Table 1; compound 10 has the following general structure:

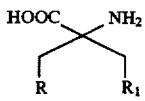

wherein the meanings for R and $R_1$ may be found in Table 1; and compounds 7, 8 and 9 have the following general structure:

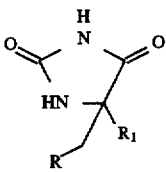

wherein the meanings for R and $R_1$ may be found in Table 1.

More specifically, the compounds according to the present invention have the structures according to the following table:

TABLE 1

| No. | substituents R = $R_1$ | antiviral activity (µM) | | | |
|---|---|---|---|---|---|
| | | CEM | | Mt-2 | |
| | | IC50 | TC25 | IC50 | TC25 |
| 2 | $SCH_2Ph$ | — | NT | 17 | NT |
| 3 | SH | 0.6 | 3 | — | 0.8 |
| 4a | $OCH_2Ph$ | — | >100 | — | 87 |
| 4b | $SCH_2C_6H_{11}$ | — | 8 | — | 12 |
| 4c | $SCH_2C_6H_4$-p-Br | — | 16 | — | 7 |
| 4d | $SCH_2C_6H_4$-p-OMe | 23 | 6 | — | 6 |

TABLE 1-continued

| 4e | $SCH_2C_6H_4$-p-CN | 25 | 15 | — | 8 |
|---|---|---|---|---|---|
| 4f | $SCH_2C_6H_4$-p-COOH | — | NT | — | NT |
| 4g | $SCH_2C_6H_4$-p-COOMe | — | 25 | — | 10 |
| 4h | $SCH_2C_6H_4$-p-$NO_2$ | 19 | 9 | — | 5 |
| 4i | $SCH_2$-pyridyl | 53 | NT | — | 45 |
| 4j | $SCH_2$-pyridyl | — | NT | — | 45 |
| 4k | $SCH_2$-pyridyl | — | NT | 81 | NT |
| 4l | $CH_2S$-naphthyl | — | NT | — | NT |
| 4m | $SCH_2$-thienyl | — | NT | — | 17 |
| 4n | $SCH_2C_6H_4$-p-$NH_2$ | 88 | NT | 6 | 16 |
| 4o | SC(O)Ph | 7 | 31 | — | 5 |
| 5a | pyridyl | — | NT | — | NT |
| 5b | Ph | — | 64 | — | 50 |
| 6 | $SCH_2Ph$ | — | 16 | — | 16 |
| 10 | $SCH_2Ph$ | — | NT | — | 60 |
| 7 | R = $SCH_2Ph$, $R_1$ = H | — | 5 | — | 2 |
| 8 | R = $SCH_2Ph$, $R_1$ = $CH_2SH$ | — | 34 | — | 50 |
| 9 | R = $SCH_2Ph$, $R_1$ = $CH_2S(CH_2)_2OH$ | — | NT | — | NT |

In the above table, "IC50" is the minimum drug concentration (µM) that inhibited CPE by 50%, calculated by using a regression analysis program for semilog curve fitting; "TC25" is the minimum drug concentration (µM) that reduced cell viability by 25%; "—" indicates the compound was inactive; "NT" indicates the compound was nontoxic up to 100 µM. With respect to the ">100" value for compound 4a, this indicates that the compound was showing toxicity, however the TC25 was greater than 100 µM, the highest concentration tested.

In the above table, compounds having moieties such those found in Compounds 2, 4b, and 4i-m, for example, are considered to have thiomethyl cyclic substituents; compounds having moieties such as those found in Compounds 4c-4h, and 4n, for example, are considered to have thiomethyl substituted cyclic moieties; compounds having moieties such as those found in Compound 9, for example, are considered to have mixed thiomethyl cyclic and thio-aliphatic moieties; and compounds such as 5a and 5b are considered to have cyclic moieties. In addition, certain compounds within the scope of the present invention may have hydrogen (such as Compound 7) or thioalkyl cyclic moieties (such as Compound 14).

A more complete and thorough understanding of the compounds and uses of the present invention may be had by reference to the following detailed examples and description.

EXAMPLE I

This example depicts the procedure for making 5,5-Bis (thiomethyl)-2,4-imidazolidinedione of compound 3.

Compound 2 (55.4 g, 0.15 mol) was placed in liquid ammonia (ca 400 ml), and fresh sodium pieces were added until a blue endpoint was reached (this reaction requires overhead stirring). After 10 minutes of permanent blue coloration, ammonium chloride was added to discharge the blue color. The ammonia was allowed to evaporate overnight under a stream of nitrogen gas. The residue was taken up in 200 ml of degassed water, chilled, acidified with concentrated HCl, and evaporated to dryness. The compound was preadsorbed on silica gel and chromatographed (13.5×12 cm, silica gel 60, 70–230 mesh) eluting with 97:3 $CHCl_3$—MeOH to give 15.5 gram of the crude compound. Trituration with 97:3 $CHCl_3$—MeOH gave (in several crops) 13.26 gram (48% yield) of compound 3; melting point 192°–194° C.

EXAMPLE II

This example depicts the procedure for making 5,5-Bis [(phenylmethoxy)methyl]-2,4-imidazolidinedione of compound 4a.

Compound 4a was prepared by reacting the symmetrical ketone 1,3-bis(benzyloxy)acetone (2.0 g, 7.4 mmol) with potassium cyanide (0.72 g, 11.1 mmol) and ammonium carbonate (4.4 g, 45.8 mmol) according to the procedure of Shen and Walford [see U.S. Pat. No. 3,547,948, Chem. Abst.75:6336j (1971)]. Upon filtration and chromatography of the resulting oil on a 2×20 cm column of silica gel, the titled compound was obtained as a white solid, 1.01 g (40% yield); melting point 73°–74° C.

The general method for the preparation of hydantoins 4b-m of the present invention involved the generation of a 0.05–0.1M solution of the trianion of hydantoin 3 by adding compound 3 to a deoxygenated solution of NaOEt (3 equivalents, prepared from Na and EtOH) in EtOH under nitrogen. The resulting clear solution was stirred for 15 minutes before the requisite alkylating agent was added all at once. The reaction mixture was stirred for 24 hrs with gradual precipitation of the reaction salts. Using 1N HCl, the pH was adjusted to between 7 and 8, the salts were filtered off, the filtrate was condensed, and the residue was chromatographed on silica gel 60 (230–400 mesh) with $CHCl_3$—MeOH mixtures as eluant. The products were analyzed as such or crystallized from the indicated solvent(s). In this manner, the following compounds were obtained:

EXAMPLE III

This example depicts the procedure for making 5,5-Bis [[(cyclohexylmethyl)thio]methyl]-2,4-imidazolidinedione of compound 4b.

Starting materials were 0.2 g (1.04 mmol) of compound 3, and 0.37 g (2.08 mmol) of (bromomethyl)cyclohexane (Fluka Chemika-BioChemika). After chromatography on a 2×20 cm column of silica gel, the desired compound was obtained as a white solid; 110 mg (26% yield); melting point 210°–212° C.

EXAMPLE IV

This example depicts the procedure for making 5,5-Bis [[[(p-bromophenyl)methyl]thio]methyl]-2,4-imidazolidinedione of compound 4c.

Starting materials were 0.3 g (1.56 mmol) of compound 3 and 0.78 (3.12 mmol) of 4-bromobenzyl bromide (Aldrich Chemical). After chromatography on a 2×20 cm column of silica gel, the desired compound was obtained as a white solid; 500 mg (61% yield); melting point 135°–137° C.

EXAMPLE V

This example depicts the procedure for making 5,5-Bis [[[(p-methoxyphenyl)methyl]thio]methyl]-2,4-imidazolidinedione of compound 4d.

Starting materials were 0.3 g (1.58 mmol) of compound 3 and 0.49 g (3.1 mmol) of 4-methoxybenzyl chloride (Aldrich). After chromatography on a 2×20 cm column of silica gel, the desired compound was obtained as a white solid; 400 mg (59% yield); melting point 122°–124° C.

EXAMPLE VI

This example depicts the procedure for making 5,5-Bis [[[(p-cyanophenyl)methyl]thio]methyl]-2,4-imidazolidinedione of compound 4e.

Starting materials were 0.3 (1.58 mmol) of compound 3, and 0.61 g (3.1 mmol) of α-bromo-p-tolunitrile (Aldrich). After chromatography on a 2×20 cm column of silica gel, the desired compound was obtained as a white solid; 50 mg (8% yield); melting point 164°–165° C.

EXAMPLE VII

This example depicts the procedure for making 5,5-Bis [[[(p-carboxyphenyl)methyl]thio]methyl]-2,4-imidazolidinedione of compound 4f.

Starting materials were 0.1 g (0.52 mmol) of compound 3, and 0.2 g (1.04 mmol) of α-bromo-p-toluic acid (Aldrich). After chromatography on a 2×20 cm column of silica gel, the desired compound was obtained as a white solid; 90 mg (37% yield); melting point 240°–242° C.

EXAMPLE VIII

This example depicts the procedure for making 5,5-Bis [[[[(p-methoxycarbonyl)phenyl]methyl]thio]methyl]-2,4-imidazolidinedione of compound 4g.

Starting materials were 0.3 g (1.56 mmol) of compound 3, and 0.71 g (3.1 mmol) of methyl 4-(bromomethyl)benzoate (Aldrich). After chromatography on a 2×20 column of silica gel, the desired compound was obtained as a white solid; 300 mg (40% yield); melting point 154°–155° C.

EXAMPLE IX

This example depicts the procedure for making 5,5-Bis [[[(p-nitrophenyl)methyl]thio]methyl]-2,4-imidazolidinedione of compound 4h.

Starting materials were 0.3 g (1.56 mmol) of compound 3, and 0.67 g (3.12 mmol) of a-bromo-p-nitrotoluene (Eastman Kodak). After chromatography on a 2×20 cm column of silica gel, the desired compound was obtained as a white solid; 130 mg (18% yield); melting point of 154°–155° C.

EXAMPLE X

This example depicts the procedure for making 5,5-Bis [[(4-pyridylmethyl)thio]methyl]-2,4-imidazolidinedione of compound 4i.

Starting materials were 0.1 g (0.52 mmol) of compound 3, and 0.17 g (1.04 mmol) of 4-picolyl chloride hydrochloride (Aldrich). After chromatography on a 2×20 cm column of silica gel, the desired compound was obtained as a white solid; 110 mg (18% yield); melting point 193°–195° C.

EXAMPLE XI

This example depicts the procedure for making 5,5-Bis [[(3-pyridylmethyl)thio]methyl]-2,4-imidazolidinedione of compound 4j.

Starting materials were 0.3 g (1.58 mmol) of compound 3, and 0.51 g (3.12 mmol) of 3-picolyl chloride hydrochloride (Aldrich). After chromatography on a 2×20 cm column of silica gel, the desired compound was obtained as a white solid; 150 mg (26% yield); melting point 121°–122° C. dec.

EXAMPLE XII

This example depicts the procedure for making 5,5-Bis [[(2-pyridylmethyl)thio]methyl]-2,-4-imidazolidinedione of compound 4k.

Starting materials were 0.3 g (1.56 mmol) of compound 3 and 0.51 g (3.12 mmol) of 2-picolyl chloride hydrochloride (Aldrich). After chromatography on a 2×20 cm column of silica gel, the desired compound was obtained as a white solid; 360 mg (62% yield); melting point 193°–195° C. dec.

EXAMPLE XIII

This example depicts the procedure for making 5,5-Bis [[(1-naphthylmethyl)thio]methyl]-2,4-imidazilidinedione of compound 4l.

Starting materials were 0.3 g (1.56 mmol) of 3 and 0.55 g (3.1 mmol) of 1-chloromethyl naphthalene (Aldrich). After chromatography on a 2×20 cm column of silica gel, the desired compound was obtained as a white solid; 220 mg (30% yield); melting point 174° C.

EXAMPLE XIV

This example depicts the procedure for making 5,5-Bis [[(2-thienylmethyl)thio]methyl]-2,4-imidazolidinedione of compound 4m.

Starting materials were 0.3 g (1.56 mmol) of compound 3 and 0.41 g (3.1 mmol) of 2-chloromethylthiophene [see Org. Syn. Col Vol III:197 (1955)]. After chromatography on a 2.5×20 cm column of silica gel, compound 4m was obtained as a white solid; 200 mg (33% yield), melting point 170°–172.50° C.

EXAMPLE XV

This example depicts the procedure for making 5,5-Bis [[(p-aminophenylmethyl)thio]methyl]-2,4-imidazilidinedione dihydrochloride of compound 4n.

A mixture of compound 4h (0.3 g, 0.65 mmol), concentrated HCL (10 ml), and granular tin (0.15 g, 30 mesh) was heated to 100° C. until the solution became transparent. The reaction was then allowed to cool and stirred at room temperature for 24 h. The solution was made basic with concentrated NH$_4$OH, the precipitate filtered, and the filtrate condensed in vacuo. Because the reaction salts trapped some of the product, they were combined with the condensed filtrate and chromatographed on silica gel (2.5×20 cm column) eluting with 95:5 CHCl$_3$—MeOH. The product-containing fractions were condensed and the residue was converted to the dihydrochloride salt by dissolving in EtOH and adding ethanolic HCl. The solvents were decanted, and the product (extremely hygroscopic) was dried in vacuo to give 160 mg (50% yield) of an orange glass, melting point 280° C. dec.

EXAMPLE XVI

This example depicts the procedure for making 5,5-Bis [(S-benzoylthio)methyl]-2,4-imidazolidinedione of compound 4o.

Compound 3 (0.25 g, 1.3 mmol) was dissolved in degassed pyridine (5 ml). The solution was cooled (10° C.) and benzoyl chloride (0.3 ml, 2.6 mmol) was added under a nitrogen atmosphere. The reaction mixture was stirred overnight at room temperature and then poured into ice-water. The resulting mixture was extracted twice with ethyl acetate and the combined extracts were washed with dilute hydrochloric acid and then saturated sodium bicarbonate solution. The organic layer was dried over anhydrous sodium sulfate, azeotroped with toluene to remove pyridine, and evaporated to a gum that was chromatographed on a 2×20 cm column of silica gel with chloroform. The resulting white powder was triturated with ether/petroleum ether (35°–60° C.) to give the desired compound (0.19 g, 36% yield), melting point 188.5°–189.5° C.

EXAMPLE XVII

This example depicts the procedure for making 5,5-Bis [(4-pyridylthio)methyl]-2,4-imidazolidinedione of compound 5a.

Compound 5a was prepared in a fashion analogous to compound 2 by reacting 1,3-dichloroacetone (1.0 g, 7.9 mmol) with 4-mercaptopyridine (1.76 g, 15.8 mmol) and then, after workup, reacting the resulting ketone with potassium cyanide (0.74 g, 11.4 mmol) and ammonium carbonate (6.45 g, 67.2 mmol) according to the published protocols [see U.S. Pat. No. 3,547,948]. After chromatography on a 2×20 cm column of silica gel and recrystallization from ethanol, the desired compound was obtained as colorless needles (320 mg, 12% yield); melting point 235°–236° C.

EXAMPLE XVIII

This example depicts the procedure for making 5,5-Bis [(phenylthio)methyl]-2,4-imidazolidinedione of compound 5b.

The desired compound was prepared in a fashion analogous to compound 2 by reacting 1,3-dichloroacetone (1.5 g, 11.8 mmol) with thiophenol (2.42 ml, 23.6 mmol) and then reacting the resulting symmetrical ketone with potassium cyanide (1.0 g, 15.4 mmol) and ammonium carbonate (4 g, 41.7 mmol) according to published protocols [see U.S. Pat. No. 3,547,948]. Upon cooling, a yellowish-brown solid precipitated that was filtered, washed with water and ethanol, and then crystallized from ethanol to give 3.28 g (81% yield), melting point 155°–156° C.

EXAMPLE XIX

This example depicts the procedure for making 5,5-Bis [(benzylthio)methyl]-2,4-imidazolidinedithione of compound 6.

Compound 2 (0.4 g, 1.07 mmol) and 1.9 g (4.29 mmol) of finely ground phosphorus pentasulfide was refluxed 2 days in toluene (15 ml). After cooling, the reaction mixture was preadsorbed on 230–400 mesh silica gel and chromatographed on silica gel (2.0×20.0 cm column) eluting with chloroform. The product-containing fractions were combined and condensed in vacuo. The residue crystallized from ether/petroleum ether (35°–50° C.) to give the desired compound as a yellow powder (80 mg, 19% yield); melting point 130° C.

EXAMPLE XX

This example depicts the procedure for making 5-[(Benzylthio)methyl]-2,4-imidazolidinedione of compound 7.

The desired compound was synthesized from S-benzyl-L-cysteine (2 g, 9.48 mmol) (Fluka) and potassium cyanate (1.7 g, 21 mmol) by a modification of published protocols [see Coll. Czech Chem. Commun. 33:2918 (1968)]. Instead of isolating the N-carbamyl-S-benzylcysteine intermediate, after an initial reflux of 1 h, 25 ml of 10% hydrochloric acid was added and reflux was continued for 1.5 h. Upon cooling, the desired product precipitated as a white solid 1.7 g (77% yield), melting point 119.5°–120.5° C.

EXAMPLE XXI

This example depicts the procedure for making 5-[(S-Benzylthio)methyl]-5-(mercaptomethyl)-2,4-imidazolidinedione of compound 8.

Compound 3 (0.60 g, 3.1 mmol) was dissolved at room temperature under $N_2$ in a solution made from sodium metal (143 mg, 6.2 mmol) in degassed, absolute ethanol (30 ml). Benzyl bromide (0.4 ml, 0.58 g, 3.4 mmol) was syringed dropwise into the reaction mixture, and the resulting yellow solution was then stirred at room temperature overnight. The solvent was removed, and the crude product was preadsorbed on silica gel and chromatographed (2×25 cm) using 98:2 chloroform-methanol as the eluant. After evaporation of the solvent, the desired compound was crystallized from ether/petroleum ether (35°–60° C.) as a white solid (0.16 g, 18% yield); melting point 119°–120° C.

EXAMPLE XXII

This example depicts the procedure for making 5-[[(Phenylmethyl)thio]methyl]-5-[[(2-(hydroxyethyl)-thio]methyl]-2,4-imidazolidinedione of compound 9.

Compound 8 (0.2 g, 0.71 mmol) was dissolved at room temperature under $N_2$ in a solution made from sodium metal (37.6 mg, 1.6 mmol) in degassed absolute ethanol (10 ml). 2-Bromoethanol (0.06 ml, 0.8 mmol) was syringed into the reaction mixture, which was then stirred at room temperature under a nitrogen atmosphere for 3 days. The solvent was evaporated and the crude product was preadsorbed on silica gel and chromatographed (2×25 cm column) on silica gel, eluting with chloroform-methanol (98:2, followed by 95:5). The product-containing fractions were evaporated to give the desired compound as a white solid (0.17 g, 74% yield); melting point 129°–132° C.

EXAMPLE XXIII

This example depicts the procedure for making 2,2-bis [(benzylthio)methyl]glycine of compound 10.

Compound 10 was resynthesized by published methods [see U.S. Pat. No. 3,547,948] by heating compound 2 (107.3 g, 0.29 mmol) and barium hydroxide monohydrate (331.7 g, 1.75 mmol) in water (2680 ml) at reflux for 192 h. The product was precipitated by acidifying the cooled solution with concentrated HCl. Filtration and drying gave 59.3 g (54% yield) of the desired product as its dihydrate. Crystallization of a small portion from ethanol gave the desired product as a white powder; melting point 205°–207° C.

EXAMPLE XXIV

This example depicts the procedure for making 5,5-bis [(phenylmethyl)thiomethyl] imidazolidinones of still another compound according to the present invention which have the structure:

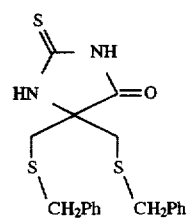

0.4 g of compound 2 (1.07 mmol) and 0.96 g (2.16 mmol) of finely ground phosphorus pentasulfide was refluxed for 1.5 hours in toluene (20 ml). After cooling, the reaction mixture was preadsorbed on 230–400 mesh silica gel and chromatographed on silica gel (2.0×20.0 cm column), eluting with 6:1 cyclohexane/ethyl acetate solvent. After collecting a forerun containing compound 6, 60 mg (14%) of the titled compound was eluted which was recrystallized from cyclohexane/ethyl acetate to provide an analytical sample with a melting point of 148°–149° C.

The compounds synthesized in this study were tested for their ability to inhibit HIV-induced cell killing and virus production in mammalian (human) cells, specifically CEM or MT-2 cell lines. The latter were added to each well of a 96-well round-bottomed microtiter plate at $5 \times 10^3$ cells per well. The cells were infected with virus at multiplicity of infection (MOI; that is the ratio of the number of virus particles to the number of cells) predetermined to give complete cell killing at 6 days postinfection. The multiplicity of infection of HIV-$1_{RF}$ utilized in these experiments was 0.01 with CEM cells and 0.005 with MT-2 cells. Serial half-log dilutions, a total of five for each compound, starting from a high test concentration of 100 μM, were added to appropriate wells in triplicate to evaluate their potential to inhibit the virus. Controls for each assay included drug cytotoxicity control (cells+drug), virus control (cells+virus), cell viability control (cells only), and drug calorimetric control (drug only). AZT was run in parallel as a positive control compound. Following 6 days of incubation at 37° C., the viability of the cells in each well was determined spectrophotometrically according to the XTT method as described by Weislow [see J. Natl Cancer Inst. 81:577 (1989)]. The data obtained from this 'acute' screen of compounds is contained In Table 1.

In addition to the 'acute' cell screening results reported in Table 1, a 'chronic' cell screening of the compounds according to the present invention has also been conducted. In this series of experiments, compound 4i, that is the disubstituted hydantoin according to the present invention with the structure:

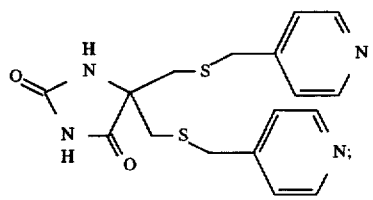

compound 4d, that is the disubstituted hydantoin according to the present invention with the structure:

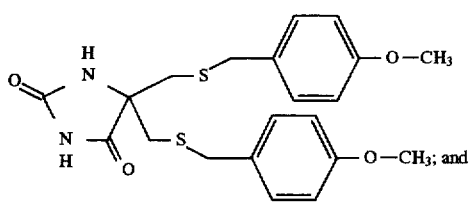

compound 11, that is the disubstituted hydantoin according to the present invention with the structure:

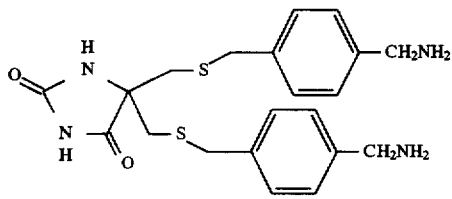

were selected as being representative of the class of compounds according to the present invention and evaluated for their capability to reduce virus production from chronically infected CEM-SS cells. Endpoints evaluated included the production of intracellular p24 as measured by flow cytometry, and the the ability of the cells to form syncytia, when co-cultured with uninfected CEM-SS cells, measured by light microscopy. These studies were run in accordance with the following example:

EXAMPLE XXV

Uninfected and chronically HIV-infected CEM-SS cells obtained as a survivor cell population following acute infection of CEM cells with the SK-1 strain of HIV-1 were maintained and routinely passaged in RPMI 1640 tissue culture medium supplemented with 10% fetal bovine serum with penicillin, streptomycin, and glutamine added.

The compounds screened were solubilized at 400 times their final concentration in DMSO; intermediate dilutions screened were also prepared in DMSO. Final dilutions for use in the screen were made into tissue culture medium.

The chronically infected cells were cultured in the continuous presence of the screening compounds for up to 7 weeks. Cells were passaged twice weekly at 1:10 dilution, and fresh compound was added at each exchange of medium. Each week the percentage of cells expressing the HIV-1 capsid protein (p24) was evaluated by flow cytometry.

One million chronically infected lymphocytes cultured in the presence and absence of antiviral compound were centrifuged in a 15 ml conical centrifuge tube, and the cellular pellet was washed to remove tissue culture medium. The washed cells were resuspended in lysolecithin/paraformaldehyde for 2 minutes at room temperature, washed, incubated with methanol for 15 minutes on ice, and washed again prior to immunofluorescent staining. The cells were incubated with the appropriate antigen specific (for example Coulter Cytometry monoclonal anti-p24) or control monoclonal antibody either for 30 minutes at 4° C. plus 0.1% sodium azide diluted in PBS containing 1% bovine serum albumin, or for 15 minutes at room temperature. The antibodies used were conjugated with phycoerythrin. Following staining, the cells were washed and the percentage of cells expressing p24 was calculated by flow cytometric analysis.

The effect of those representative compounds according to the present invention on the inhibition of p24 expression on chronically infected CEM cells is tabulated below (ND= not done):

| concentration | | percentage p24 positive week of continuous treatment | | | | | | |
|---|---|---|---|---|---|---|---|---|
| Compound: | µg/ml | 1 | 2 | 3 | 4 | 5 | 6 | 7 |
| none | | ND | 100 | 100 | 100 | 100 | 100 | 100 |
| 11 | 50 | ND | ND | ND | ND | ND | ND | ND |
|  | 25 | ND | 42 | 42 | 65 | 15 | 50 | 7 |
|  | 10 | ND | 55 | 74 | 87 | 42 | 53 | 10 |
| 4(d) | 50 | ND | 17 | ND | ND | 100 | ND |  |
|  | 25 | ND | 54 | 95 | ND | 71 | ND |  |
|  | 10 | ND | 58 | 97 | ND | 56 | ND | 2 |
| 4(i) | 50 | ND | 45 | 66 | 45 | 29 | 43 | 20 |
|  | 25 | ND | 40 | 52 | 72 | 58 | 63 | 30 |
|  | 10 | ND | 36 | 80 | 78 | 52 | 63 | 35 |

As tabulated above, each of the representative compounds induced a reduction in the percentage of cells expressing p24 as detected by flow cytometric analysis. The results of these assays, however, indicate some variability in the level of reduction of expression. These results indicate that the compounds reduce the percentage of cells expressing p24, but also demonstrate that the cells which continue to produce p24 continue to produce the same amount of protein, i.e., there was no change in fluorescence intensity.

Preparation of cells for syncytium formation screening was conducted in accordance with the following protocol:

EXAMPLE XXVI

A second aliquot of cells was washed and resuspended in tissue culture medium at $1 \times 10^6$ cells per ml of medium. The chronically infected cells were co-cultured with $1 \times 10^5$ uninfected CEM-SS cells at serial ten-fold dilutions ranging from $10^5$ cells to $10^1$ cells per well in a 96-well round-bottom microtiter tissue culture plate. At 24 and 48 hours after co-cultivation the number of syncytia were quantitated in each well by microscopic observation of each well.

The effect of those representative compounds according to the present invention on the ability of chronically infected CEM cells to form syncytia is tabulated below (ND=not done):

| concentration | | percentage of syncytia formation week of continuous treatment | | | | | | |
|---|---|---|---|---|---|---|---|---|
| Compound: | µg/ml | 1 | 2 | 3 | 4 | 5 | 6 | 7 |
| none | | 100 | 100 | 100 | 100 | 100 | 100 | 100 |
| 11 | 50 | 32 | ND | ND | ND | ND | ND | ND |
|  | 25 | 28 | 36 | 60 | 34 | ND | 27 | 31 |
|  | 10 | 100 | 39 | 40 | 130 | ND | 126 | 52 |
| 4(d) | 50 | 30 | 0 | ND | ND | ND | 2 | ND |
|  | 25 | 38 | 32 | 24 | ND | ND | 6 | ND |
|  | 10 | 100 | 80 | 4 | ND | ND | 2 | 7 |
| 4(i) | 50 | 100 | 73 | 25 | 18 | ND | 20 | 2 |
|  | 25 | 100 | 68 | 41 | 52 | ND | 14 | 8 |
|  | 10 | 92 | 61 | 15 | 120 | ND | 51 | 21 |

The results of the syncytial experiments tabulated above indicate that the representative compounds induced a reduction in the percentage of cells producing virus, with the greatest reduction in syncytium formation being obtained with compound 4(d). However, compound 4(i) induced a significant reduction in syncytium formation in the absence of any detectable toxicity. Similar results have been found with other compounds according to the present Invention.

Among the strategies that were incorporated into the design of the analogue compounds according to the present invention were (1) substitution of oxygen for sulfur in the side chains emanating from the hydantoin 5-position (e.g., compound 4a); (2) removal of one of the substituents of the 5-position (e.g., compound 7); (3) varying the length of these substituents (e.g., compounds 5a and b); (4) removal of one or both alkyl groups capping sulfur on the side chains (e.g., compounds 3 and 8); (5) saturation of the aromatic ring in the side chains (e.g., compound 4b); (6) and varying the substituent on, or the nature of, the aromatic ring (e.g., compounds 4c-n, 11-13 and 15); (7) extending the length of one or both alkyl groups capping sulfur on the side chains (e.g., compounds 9, 14 and 16); and (8) replacement of the alkyl groups capping sulfur on the side chains with carbonyl (e.g., compound 4a). Very little was done to modify the hydantoin ring except to replace one or both of the oxygen atoms with sulfur (compound 6 and example XXIV)) and to hydrolyze the ring completely to a disubstituted glycine derivative (compound 10). These strategies can easily be applied to other members of the class of compounds according to the present invention, and these analogue compounds are deemed to be within the scope and claimed subject matter of the present invention.

Thus, while we have illustrated and described the preferred embodiment of our invention, it is to be understood that this invention is capable of further variation and modification, and we therefore do not wish to be limited to the precise terms set forth, but desire to avail ourselves of such changes and alterations which may be made for adapting the invention to various usages and conditions. For example, as Indicated in Table 1 the disubstituted moieties R and R₁ are conventionally the same in many instances, however, they need not be, and R may be the same as R₁ or it may be a selected from other moieties listed in Table 1. In addition, the sulfur atoms in each of the moieties listed in Table 1 may also be replaced with oxygen (as for example seen for compound 4a), which may also be derivatized, or with other heteroatoms, such as nitrogen, which themselves may be derivatized. Furthermore, certain additional moieties not listed in the Table are within the scope of the present invention, for example, moieties with the structures:

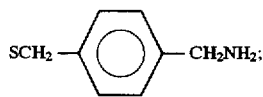 (11)

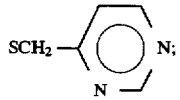 (12)

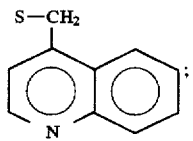 (13)

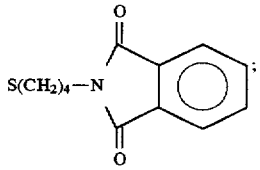 (14)

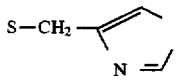 (15)

$S-(CH_2)_n-NH_2$ (16)

wherein n is an integer from 2 to 4, inclusive.

Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same;

We claim:

1. A disubstituted hydantoin of the general structure

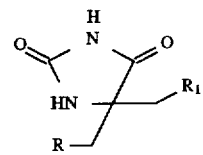

wherein R and R₁, which may be the same or different, are selected from the group consisting of thiomethyl cyclic, thiomethyl substituted cyclics, thioaliphatics, thioalkyl cyclics and mixtures thereof, with the proviso that the disubstituted hydantoin is not 5,5-bis-benzylthiomethyl hydantoin.

2. A disubstituted hydantoin according to claim 1 wherein R and R1 are selected from the group consisting of $S-CH_2-C_6H_4-p-CH_2NH_2$;

$S-CH_2-C_6H_4-p-Br$;

$S-CH_2-C_6H_4-p-OMe$;

$S-CH_2-C_6H_4-p-CN$;

$S-CH_2-C_6H_4-p-COOH$;

$S-CH_2-C_6H_4-p-COOMe$;

$S-CH_2-C_6H_4-p-NO_2$; and $S-CH_2-C_6H_4-p-NH_2$.

3. A disubstituted hydantoin according to claim 1 wherein R and R1 are selected from the group consisting of

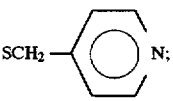

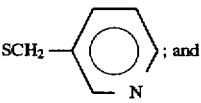

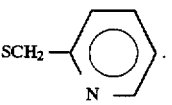

4. The disubstituted hydantoin according to claim 3 wherein R and R1 are

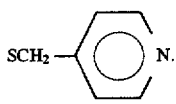

5. A disubstituted hydantoin according to claim 3 wherein R and R1 are

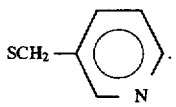

6. A disubstituted hydantoin according to claim 3 wherein R and R1 are

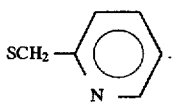

7. A disubstituted hydantoin according to claim 1 wherein R and R1 are selected from the group consisting of

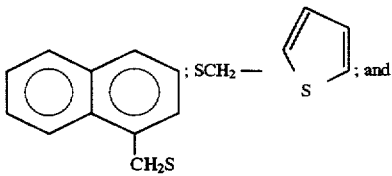

S—CH$_2$—C$_6$H$_{11}$.

8. A disubstituted hydantoin according to claim 1 wherein each of R and R1 are thiomethyl cyclic moieties that are substituted on the cyclic moiety.

9. A disubstituted hydantoin according to claim 1 wherein R and R1 are selected from the group consisting of:

—O—CH$_2$—Ph;

—S—C(O)—Ph;

—S—Ph; and

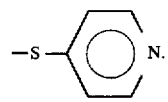

10. A disubstituted hydantoin of the general structure

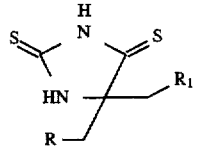

wherein R and R$_1$ are S—CH$_2$—Ph.

11. A disubstituted hydantoin of the general structure

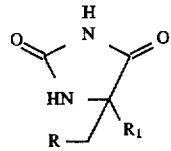

wherein R and R$_1$ which may be the same or different, are each individually selected from the group consisting of S—CH$_2$—Ph;

H;

CH$_2$—SH; and

CH$_2$—S—(CH$_2$)$_2$—OH;

with the proviso that R and R1 are not both H.

12. The disubstituted hydantoin according to claim 11 wherein R is S—CH$_2$—Ph, and R$_1$ is H.

13. The disubstituted hydantoin according to claim 11 wherein R is S—CH$_2$—Ph, and R$_1$ is CH$_2$—SH.

14. The disubstituted hydantoin according to claim 11 wherein R is S—CH$_2$—Ph, and R$_1$ is CH$_2$—S(CH$_2$)$_2$—OH.

* * * * *